United States Patent
Basey et al.

(12) 
(10) Patent No.: US 6,339,142 B1
(45) Date of Patent: Jan. 15, 2002

(54) PROTEIN PURIFICATION

(75) Inventors: Carol D. Basey, Winters; Greg S. Blank, Menlo Park, both of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/679,397

(22) Filed: Oct. 3, 2000

Related U.S. Application Data

(62) Division of application No. 09/304,465, filed on May 3, 1999
(60) Provisional application No. 60/084,459, filed on May 6, 1998.

(51) Int. Cl.$^7$ .................. A61K 39/395; C07K 16/30
(52) U.S. Cl. .................. 530/387.3; 424/133.1; 424/138.1; 424/155.1; 530/388.85
(58) Field of Search .............. 424/133.1, 138.1, 424/155.1; 530/387.3, 388.85

(56) References Cited

U.S. PATENT DOCUMENTS

| | | | |
|---|---|---|---|
| 4,966,851 A | * 10/1990 | Durance et al. | 530/416 |
| 5,110,913 A | * 5/1992 | Coan et al. | 530/416 |
| 5,112,951 A | * 5/1992 | Beidler et al. | 530/416 |
| 5,115,101 A | * 5/1992 | Bloom et al. | 530/416 |
| 5,118,796 A | * 6/1992 | Prior et al. | 530/416 |
| 5,256,769 A | * 10/1993 | Kato et al. | 530/416 |
| 5,279,823 A | * 1/1994 | Frenz et al. | 424/94.61 |
| 5,451,662 A | * 9/1995 | Navem et al. | 530/416 |
| 5,525,338 A | * 6/1996 | Goldenberg | 424/178.1 |
| 5,821,337 A | 10/1998 | Carter et al. | 530/387.3 |
| 6,005,081 A | * 12/1999 | Burton et al. | 530/416 |

FOREIGN PATENT DOCUMENTS

| | | |
|---|---|---|
| EP | 333574 | 9/1989 |
| EP | 556083 | 8/1993 |
| EP | 460426 B1 | 9/1997 |
| WO | WO 89/05157 | 6/1989 |
| WO | WO 96/33208 | 10/1996 |

OTHER PUBLICATIONS

Carter et al., "Humanization of an anti–p185$^{HER2}$ antibody for human cancer therapy" *Proc. Natl. Acad. Sci.* 89:4285–4289 (May 1992).

Gagnon, P., "Ion Exchange Chromatography" *Purification Tools for Monoclonal Antibodies*, Tucson:Validated Biosystems, Inc., Chapter 4, pp. 57–86 (1996).

Graf et al., "Ion exchange resins for the purification of monoclonal antibodies from animal cell culture" *Bioseparation* 4(1):7–20 (Feb. 1994).

Harris,R., "Chromatographic Techniques for the Characterization of Human MAbs" (Slides presented at the Waterside Monoclonal Conference held at the Omni Waterside Hotel in Harborside–Norfolk, Virginia on Apr. 22–25, 1996) pp. 1–7.

Mhatre et al., "Purification of antibody Fab fragments by cation–exchange chromatography and pH gradient elution" *Journal of Chromatography A* 707 (2) :225–231 (Jul. 21, 1995).

Neidhardt et al., "Rapid, two–step purification process for the preparation of pyrogen–free murine immunoglobulin $G_1$ monoclonal antibodies" *Journal of Chromatography* 590 (2) :255–261 (1992).

Sofer et al. *Handbook of Process Chromatography: A Guide to Optimization, Scale–up, and Validation*, San Diego:Academic Press pp. 65–80 (1997).

Tishchenko et al., "Effect of salt concentration gradient on separation of different types of specific immunoglobulins by ion–exchange chromatography on DEAE cellulose" *Journal of Chromatography B* 706 (1) :157–166 (Feb. 27, 1998).

* cited by examiner

*Primary Examiner*—David Saunders
(74) *Attorney, Agent, or Firm*—Wendy M. Lee

(57) ABSTRACT

A method for purifying a polypeptide by ion exchange chromatography is described which involves changing the conductivity and/or pH of buffers in order to resolve a polypeptide of interest from one or more contaminants.

3 Claims, 7 Drawing Sheets

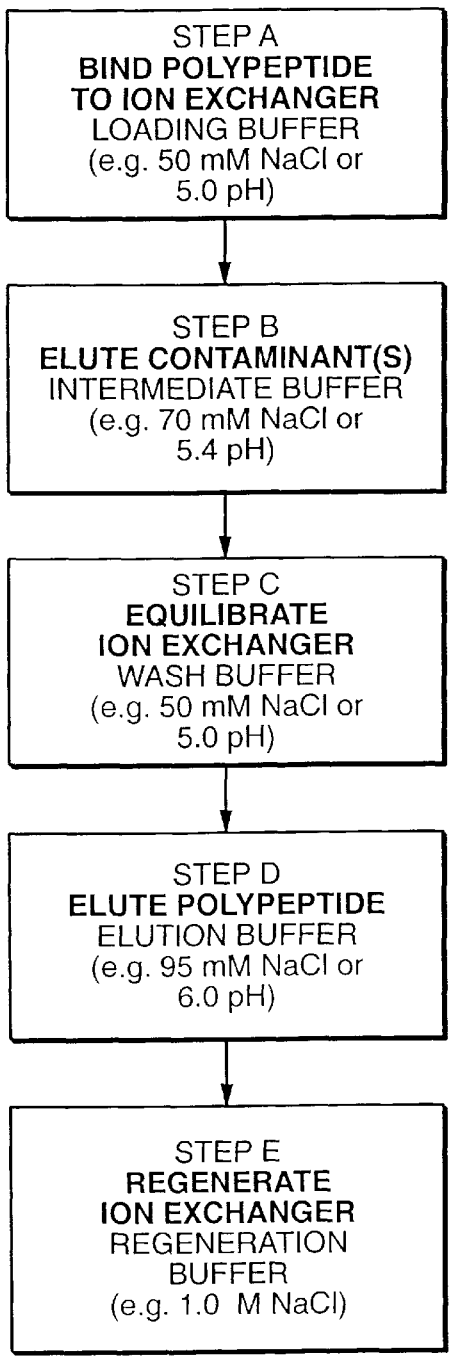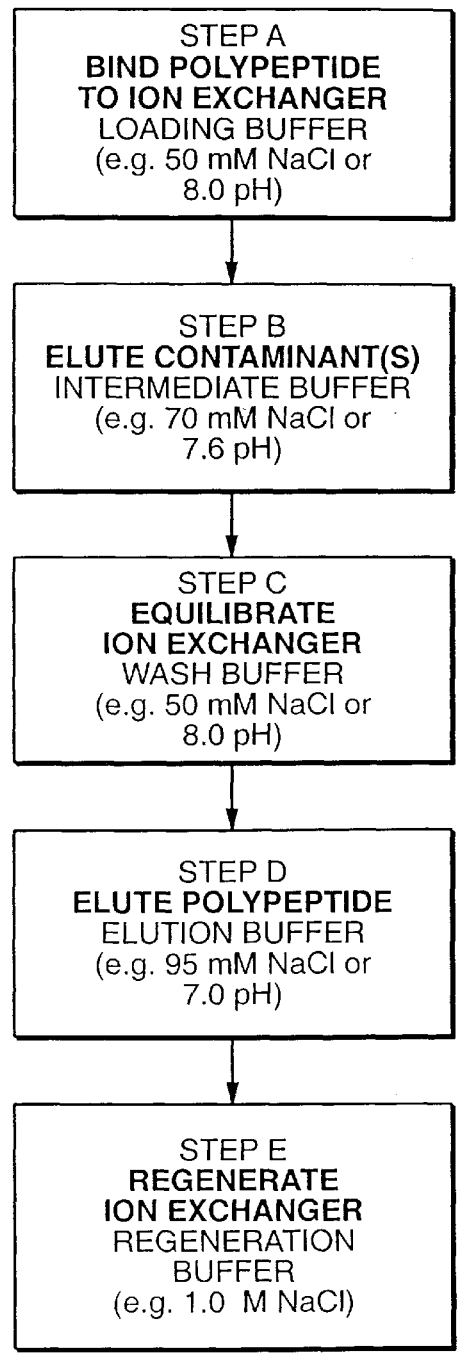
FIG._1  FIG._2

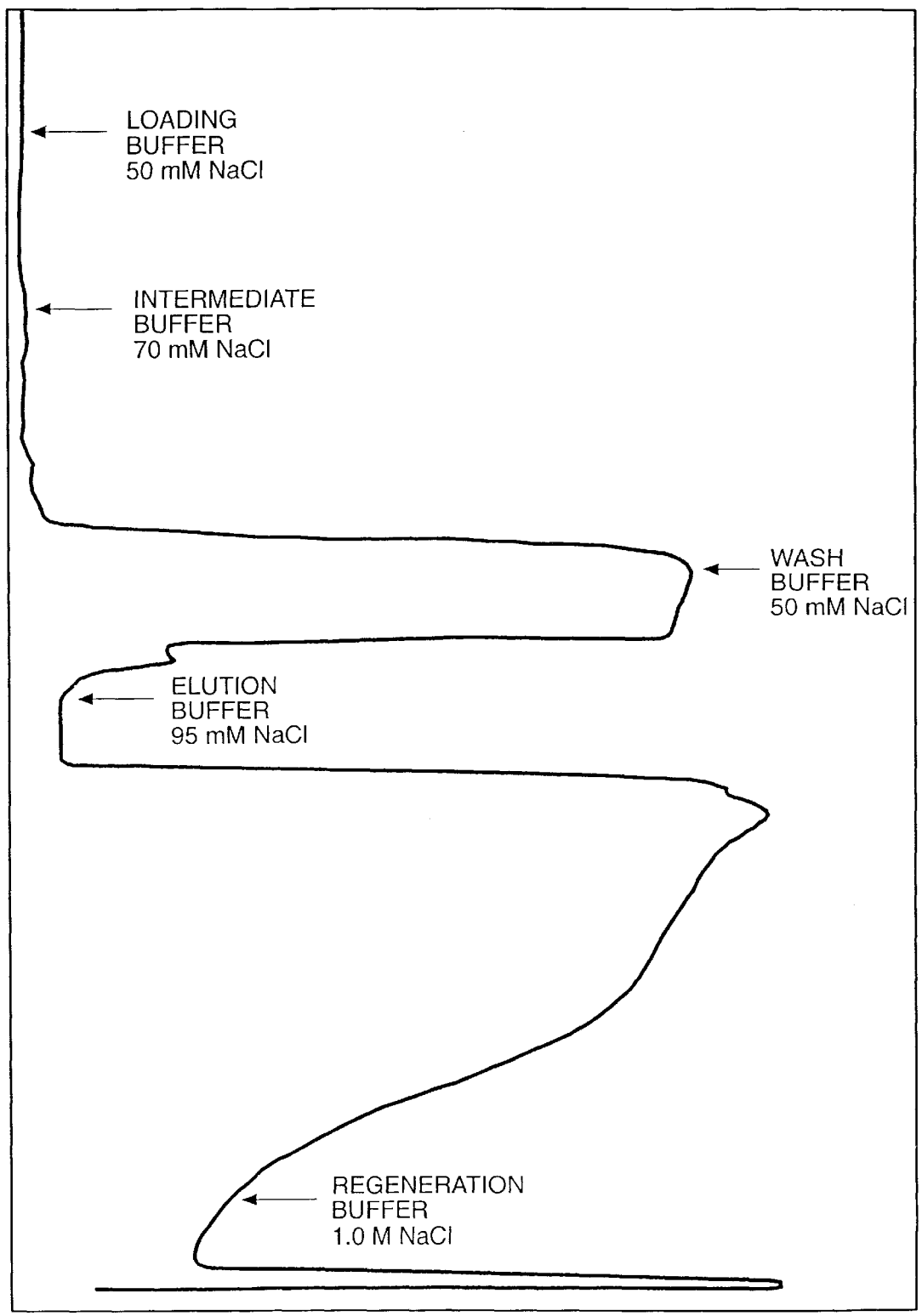
FIG._3

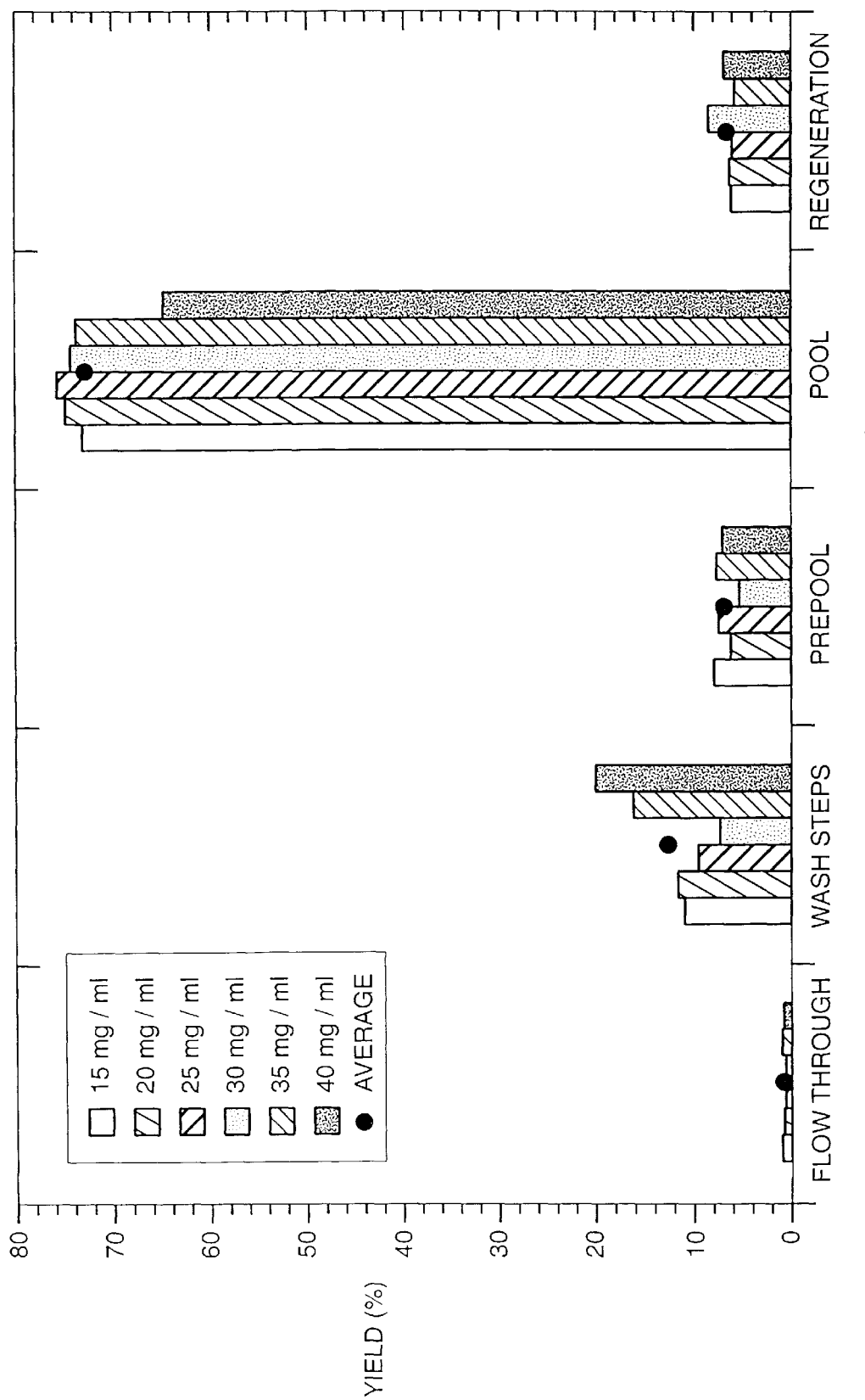
FIG._4

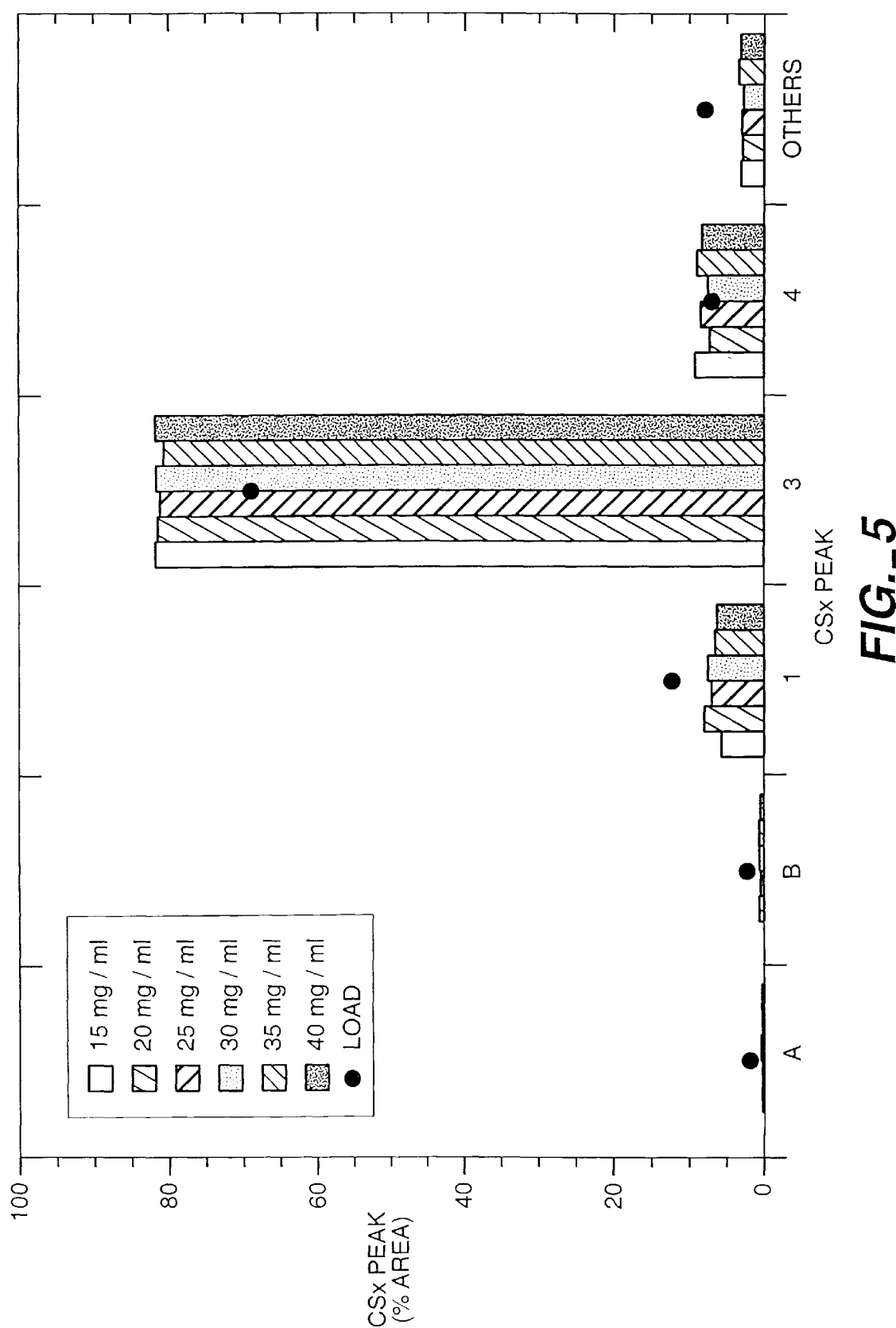
FIG._5

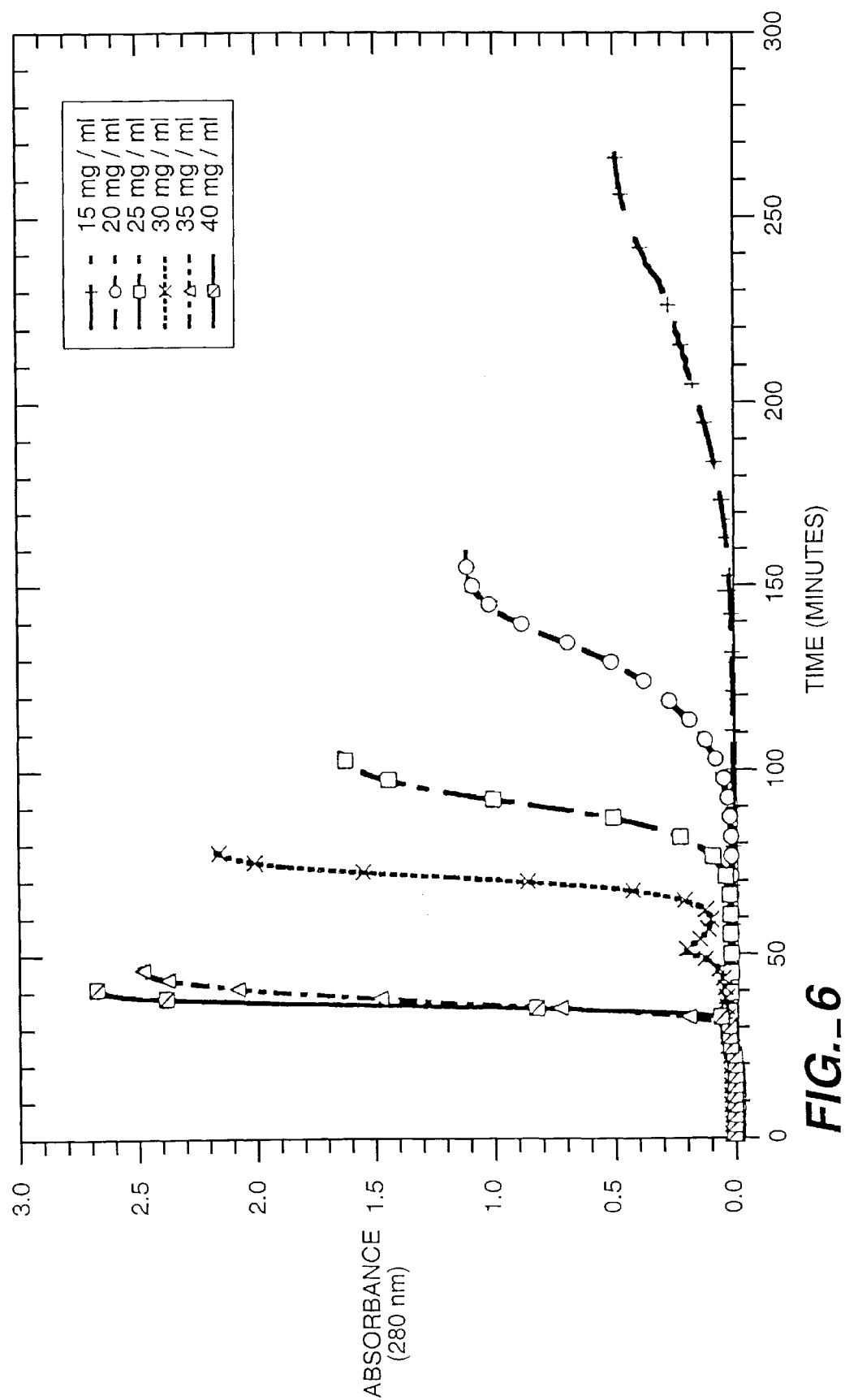
FIG._6

LIGHT CHAIN

```
  1                           15                          30                            45
  DIQMTQSPSSLSASVGDRVTITCRASQDVNTAVAWYQQKPGKAPK
 46                           60                          75                            90
  LLIYSASFLYSGVPSRFSGSRSGTDFTLTISSLQPEDFATYYCQQ
 91                          105                         120                           135
  HYTTPPTFGQGTKVEIKRTVAAPSVFIFPPSDEQLKSGTASVVCL
136                          150                         165                           180
  LNNFYPREAKVQWKVDNALQSGNSQESVTEQDSKDSTYSLSSTLT
181                          195                         210    214
  LSKADYEKHKVYACEVTHQGLSSPVTKSFNRGEC
```

HEAVY CHAIN

```
1   EVQLVESGGGLVQPGGSLRLSCAASGFNIKDTYIHWVRQAPGKGL      45
46  EWVARIYPTNGYTRYADSVKGRFTISADTSKNTAYLQMNSLRAED      90
91  TAVYYCSRWGGDGFYAMDYWGQGTLVTVSSASTKGPSVFPLAPSS     135
136 KSTSGGTAALGCLVKDYFPEPVTVSWNSGALTSGVHTFPAVLQSS     180
181 GLYSLSSVVTVPSSSLGTQTYICNVNHKPSNTKVDKKVEPKSCDK     225
226 THTCPPCPAPELLGGPSVFLFPPKPKDTLMISRTPEVTCVVVDVS     270
271 HEDPEVKFNWYVDGVEVHNAKTKPREEQYNSTYRVVSVLTVLHQD     315
316 WLNGKEYKCKVSNKALPAPIEKTISKAKGQPREPQVYTLPPSREE     360
361 MTKNQVSLTCLVKGFYPSDIAVEWESNGQPENNYKTTPPVLDSDG     405
406 SFFLYSKLTVDKSRWQQGNVFSCSVMHEALHNHYTQKSLSLSPG      449
```

PROTEIN PURIFICATION

This is a divisional of co-pending application No. 09/304,465 filed May 3, 1999 which claims priority under 35 USC §119 to provisional application No. 60/084,459 filed May 6, 1998, both disclosures of which are hereby incorporated by reference.

BACKGROUND OF THE INVENTION

1. Field of the Invention

This invention relates generally to protein purification. In particular, the invention relates to a method for purifying a polypeptide (e.g. an antibody) from a composition comprising the polypeptide and at least one contaminant using the method of ion exchange chromatography.

2. Description of Related Art

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through".

Ion exchange chromatography is a chromatographic technique that is commonly used for the purification of proteins. In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). In the past, these changes have been progressive; i.e., the pH or conductivity is increased or decreased in a single direction.

SUMMARY OF THE INVENTION

The present invention provides an ion exchange chromatographic method wherein a polypeptide of interest is bound to the ion exchange material at an initial conductivity or pH and then the ion exchange material is washed with an intermediate buffer at a different conductivity or pH, or both. At a specific point following this intermediate wash, and contrary to ion exchange chromatography standard practice, the ion exchange material is washed with a wash buffer where the change in conductivity or pH, or both, from the intermediate buffer to the wash buffer is in an opposite direction to the change in conductivity or pH, or both, achieved in the previous steps. Only after washing with the wash buffer, is the ion exchange material prepared for the polypeptide molecule of interest to be eluted by the application of the elution buffer having a conductivity or pH, or both, which differ from the conductivity or pH, or both, of the buffers used in previous steps.

This novel approach to ion exchange chromatography is particularly useful in situations where a product molecule must be separated from a very closely related contaminant molecule at full manufacturing scale, where both purity and high recovery of polypeptide product are desired.

Accordingly, the invention provides a method for purifying a polypeptide from a composition comprising the polypeptide and a contaminant, which method comprises the following steps performed sequentially:

(a) binding the polypeptide to an ion exchange material using a loading buffer, wherein the loading buffer is at a first conductivity and pH;

(b) washing the ion exchange material with an intermediate buffer at a second conductivity and/or pH so as to elute the contaminant from the ion exchange material;

(c) washing the ion exchange material with a wash buffer which is at a third conductivity and/or pH, wherein the change in conductivity and/or pH from the intermediate buffer to the wash buffer is in an opposite direction to the change in conductivity and/or pH from the loading buffer to the intermediate buffer; and (d) washing the ion exchange material with an elution buffer at a fourth conductivity and/or pH so as to elute the polypeptide from the ion exchange material. The first conductivity and/or pH may be the same as the third conductivity and/or pH.

Where the ion exchange material comprises a cation exchange resin, the conductivity and/or pH of the intermediate buffer is/are preferably greater than the conductivity and/or pH of the loading buffer; the conductivity- and/or pH of the wash buffer is/are preferably less than the conductivity and/or pH of the intermediate buffer; and the conductivity and/or pH of the elution buffer is/are preferably greater than the conductivity and/or pH of the intermediate buffer. Preferably, the conductivity and/or pH of the wash buffer is/are about the same as the conductivity and/or pH of the loading buffer.

Preferably elution of the contaminant and of the polypeptide is achieved by modifying the conductivity of the intermediate buffer and of the elution buffer, respectively, while keeping the pH of these buffers approximately the same.

The invention also provides a method for purifying a polypeptide from a composition comprising the polypeptide and a contaminant, which method comprises the following steps performed sequentially:

(a) binding the polypeptide to a cation exchange material using a loading buffer, wherein the loading buffer is at a first conductivity and pH;

(b) washing the cation exchange material with an intermediate buffer at a second conductivity and/or pH which is greater than that of the loading buffer so as to elute the contaminant from the ion exchange material;

(c) washing the cation exchange material with a wash buffer which is at a third conductivity and/or pH which is less than that of the intermediate buffer; and (d) washing the cation exchange material with an elution buffer at a fourth conductivity and/or pH which is greater than that of the intermediate buffer so as to elute the polypeptide from the ion exchange material.

In addition, the invention provides a method for purifying an antibody from a composition comprising the antibody and a contaminant, which method comprises loading the composition onto a cation exchange resin, wherein the amount of antibody loaded onto the cation exchange resin is from about 20 mg to about 35 mg of the antibody per mL of cation exchange resin and, optionally, further comprising eluting the antibody from the cation exchange resin. The method preferably further comprises an intermediate wash step for eluting one or more contaminants from the ion exchange resin. This intermediate wash step usually precedes the step of eluting the antibody.

The invention further provides a composition comprising a mixture of anti-HER2 antibody and one or more acidic variants thereof, wherein the amount of the acidic variant(s) in the composition is less than about 25% and preferably less than about 20%, e.g. in the range from about 1% to about 18%. Optionally, the composition further comprises a pharmaceutically acceptable carrier

BRIEF DESCRIPTION OF THE DRAWINGS

FIG. 1 is a flow diagram showing how one could perform cation exchange chromatography by altering conductivity (e.g. to the NaCl concentrations of Example 1 below) or by altering pH (e.g. to the pH values as shown in the flow diagram).

FIG. 2 is a flow diagram showing how one could perform anion exchange chromatography by altering conductivity (e.g. to the Nacl concentrations as depicted in the figure) or by altering pH (e.g. to the pH values as shown).

FIG. 3 is an absorbance trace from a cation exchange chromatography run of Example 1 at full manufacturing scale. Points at which the column is washed with the different buffers described herein are marked with arrows.

FIG. 4 depicts recombinant humanized anti-HER2 monoclonal antibody (rhuMAb HER2) recovered in each chromatography fraction (calculated as the percentage of the sum total of all fractions of the relevant chromatography). Flow through, wash steps, and prepool fractions are all effluent samples collected from the onset of load to the initiation of pooling. The pool fraction is the five column volume effluent sample of elution starting at the leading shoulder's inflection point. The regeneration fraction contains effluent captured from the end of pooling to the end of regeneration.

FIG. 5 shows the quality of rhuMAb HER2 in each cation exchange chromatography pool sample as evaluated by carboxy sulfon cation exchange high pressure liquid chromatography (CSx HPIEX). Peaks a, b, and 1 are deamidated forms of rhuMAb HER2. Peak 3 is nondeamidated rhuMAb HER2. Peak 4 is a combination of C-terminal Lysine containing and iso-aspartate variants of rhuMAb HER2.

FIG. 6 shows the absorbance (280 nm) profiles of the 0.025 M MES/0.070 M NaCl, pH 5.6 wash for each chromatography. The mass of rhuMAb HER2 applied to the cation exchange resin effects the peak's absorbance level at the apex as well as the amount of buffer required to reach the apex. Due to minor peaks which occur (as best seen in the 30 mg/mL load) in this wash, the apex is defined as absorbance levels of at least 0.5 absorbance units (AU).

FIGS. 7A and 7B show the amino acid sequences of humMAb4D5-8 light chain (SEQ ID NO:1) and humMAb4D5-8 heavy chain (SEQ ID NO:2), respectively.

DETAILED DESCRIPTION OF THE PREFERRED EMBODIMENTS

Definitions:

The "composition" to be purified herein comprises the polypeptide of interest and one or more contaminants. The composition may be "partially purified" (i.e. having been subjected to one or more purification steps, such as Protein A Chromatography as in Example 1 below) or may be obtained directly from a host cell or organism producing the polypeptide (e.g. the composition may comprise harvested cell culture fluid).

As used herein, "polypeptide" refers generally to peptides and proteins having more than about ten amino acids. Preferably, the polypeptide is a mammalian protein, examples of which include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides. Most preferred is a full length antibody that binds human HER2.

A "contaminant" is a material that is different from the desired polypeptide product. The contaminant may be a variant of the desired polypeptide (e.g. a deamidated variant or an amino-aspartate variant of the desired polypeptide) or another polypeptide, nucleic acid, endotoxin etc.

A "variant" or "amino acid sequence variant" of a starting polypeptide is a polypeptide that comprises an amino acid sequence different from that of the starting polypeptide. Generally, a variant will possess at least 80% sequence identity, preferably at least 90% sequence identity, more preferably at least 95% sequence identity, and most preferably at least 98% sequence identity with the native polypeptide. Percentage sequence identity is determined, for example, by the Fitch et al., *Proc. Natl. Acad. Sci. USA* 80:1382–1386 (1983), version of the algorithm described by Needleman et al., *J. Mol. Biol.* 48:443–453 (1970), after aligning the sequences to provide for maximum homology. Amino acid sequence variants of a polypeptide may be prepared by introducing appropriate nucleotide changes into DNA encoding the polypeptide, or by peptide synthesis. Such variants include, for example, deletions from, and/or insertions into and/or substitutions of, residues within the amino acid sequence of the polypeptide of interest. Any combination of deletion, insertion, and substitution is made to arrive at the final construct, provided that the final construct possesses the desired characteristics. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference, for example.

An "acidic variant" is a variant of a polypeptide of interest which is more acidic (e.g. as determined by cation exchange chromatography) than the polypeptide of interest. An example of an acidic variant is a deamidated variant.

A "deamidated" variant of a polypeptide molecule is a polypeptide wherein one or more asparagine residue(s) of the original polypeptide have been converted to aspartate, i.e. the neutral amide side chain has been converted to a residue with an overall acidic character. Deamidated humMAb4D5 antibody from the Example below has Asn30 in CDR1 of either or both of the $V_L$ regions thereof converted to aspartate. The term "deamidated human DNase" as used herein means human DNase that is deamidated at the asparagine residue that occurs at position 74 in the amino acid sequence of native mature human DNase (U.S. Pat. No. 5,279,823; expressly incorporated herein by reference).

The term "mixture" as used herein in reference to a composition comprising an anti-HER2 antibody, means the presence of both the desired anti-HER2 antibody and one or more acidic variants thereof. The acidic variants may comprise predominantly deamidated anti-HER2 antibody, with minor amounts of other acidic variant(s). It has been found, for example, that in preparations of anti-HER2 antibody obtained from recombinant expression, as much as about 25% of the anti-HER2 antibody is deamidated.

In preferred embodiments of the invention, the polypeptide is a recombinant polypeptide. A "recombinant polypeptide" is one which has been produced in a host cell which has been transformed or transfected with nucleic acid encoding the polypeptide, or produces the polypeptide as a result of homologous recombination.

"Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well a cell within a host animal. Methods for recombinant production of polypeptides are described in U.S. Pat. No. 15 5,534,615, expressly incorporated herein by reference, for example.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those polypeptides discussed above. Preferred molecular targets for antibodies encompassed by the present invention include CD polypeptides such as CD3, CD4, CD8, CD19, CD20 and CD34; members of the HER receptor family such as the EGF receptor, HER2, HER3 or HER4 receptor; cell adhesion molecules such as LFA-1, Mac1, p150,95, VLA-4, ICAM-1, VCAM and av/b3 integrin including either a or b subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). In a further embodiment, "monoclonal antibodies" can be isolated from antibody phage libraries generated using the techniques described in McCafferty et al., *Nature*, 348:552–554 (1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); Bruggermann et al., *Year in Immuno.*, 7:33 (1993); and Duchosal et al. *Nature* 355:258 (1992).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851–6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Polypeptides of Immunological Interest*, 5th Ed. Public Health Service, National Institutes of Health, Bethesda, Md. (1991)) and/or those residues from a "hypervariable loop" (i.e. residues 26–32 (L1), 50–52 (L2) and 91–96 (L3) in the light chain variable domain and 26–32 (H1), 53–55 (H2) and 96–101 (H3) in the heavy chain variable domain; Chothia and Lesk *J. Mol. Biol.* 196:901–917 (1987)). "Framework" or "FR" residues are those variable domain residues other than the hypervariable region residues as herein defined. The CDR and FR residues of the rhuMAb HER2 antibody of the example below (humAb4D5-8) are identified in Carter et al., *Proc. Natl. Acad. Sci. USA*, 89:4285 (1992).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992);Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163–167 (1992)). In another embodiment, the F(ab')$_2$ is formed using the leucine zipper GCN4 to promote assembly of the F(ab')$_2$ molecule. According to another approach, F(ab')$_2$ fragments can be isolated directly from recombinant host cell culture. Other techniques for the production of antibody fragments will be apparent to the skilled practitioner.

In other embodiments, the antibody of choice is a single chain Fv fragment (scFv). See WO 93/16185. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies,* vol. 113, Rosenburg and Moore eds. Springer-Verlag, New York, pp. 269–315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WC) 93/11161; and Hollinger et al., *Proc. Natl. Acad. Sci. USA* 90:6444–6448 (1993).

The expression "linear antibodies" when used throughout this application refers to the antibodies described in Zapata et al. *Polypeptide Eng.* 8(10):1057–1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

"Multispecific antibodies" have binding specificities for at least two different epitopes, where the epitopes are usually from different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma asso- ciated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques. Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites Another strategy for making bispecific antibody fragments by the use of single-chain Fv (sFv) diners has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

The phrase "ion exchange material" refers to a solid phase which is negatively charged (i.e. a cation exchange resin) or positively charged (i.e. an anion exchange resin). The charge may be provided by attaching one or more charged ligands to the solid phase, e.g. by covalent linking. Alternatively, or in addition, the charge may be an inherent property of the solid phase (e.g. as is the case for silica, which has an overall negative charge).

By "solid phase" is meant a non-aqueous matrix to which one or more charged ligands can adhere. The solid phase may be a purification column, a discontinuous phase of discrete particles, a membrane, or filter etc. Examples of materials for forming the solid phase include polysaccharides (such as agarose and cellulose); and other mechanically stable matrices such as silica (e.g. controlled pore glass), poly(styrenedivinyl)benzene, polyacrylamide, ceramic particles and derivatives of any of the above.

A "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methylcellulose, BAKERBOND ABX™, sulphopropyl (SP) immobilized on agarose (e.g. SP-SEPHAROSE FAST FLOW™ or SP-SEPHAROSE HIGH PERFORMANCE™, from Pharmacia) and sulphonyl immobilized on agarose (e.g. S-SEPHAROSE FAST FLOW™ from Pharmacia).

The term "anion exchange resin" is used herein to refer to a solid phase which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (Pharmacia).

A "buffer" is a solution that resists changes in pH by the action of its acid-base conjugate components. Various buffers which can be employed depending, for example, on the desired pH of the buffer are described in Buffers. *A Guide for the Preparation and Use of Buffers in Biological Systems*, Gueffroy, D., Ed. Calbiochem Corporation (1975). In one embodiment, the buffer has a pH in the range from about 5 to about 7 (e.g. as in Example 1 below). Examples of buffers that will control the pH in this range include MES, MOPS, MOPSO, phosphate, acetate, citrate, succinate, and ammonium buffers, as well as combinations of these.

The "loading buffer" is that which is used to load the composition comprising the polypeptide molecule of interest and one or more contaminants onto the ion exchange resin. The loading buffer has a conductivity and/or pH such that the polypeptide molecule of interest (and generally one or more contaminants) is/are bound to the ion exchange resin.

The "intermediate buffer" is used to elute one or more contaminants from the ion exchange resin, prior to eluting the polypeptide molecule of interest. The conductivity and/or pH of the intermediate buffer is/are such that the contaminant is eluted from the ion exchange resin, but not significant amounts of the polypeptide of interest.

The term "wash buffer" when used herein refers to a buffer used to wash or re-equilibrate the ion exchange resin, prior to eluting the polypeptide molecule of interest. Conveniently, the wash buffer and loading buffer may be the same, but this is not required.

The "elution buffer" is used to elute the polypeptide of interest from the solid phase. The conductivity and/or pH of the elution buffer is/are such that the polypeptide of interest is eluted from the ion exchange resin.

A "regeneration buffer" may be used to regenerate the ion exchange resin such that it can be re-used. The regeneration buffer has a conductivity and/or pH as required to remove substantially all contaminants and the polypeptide of interest from the ion exchange resin.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is mmhos (mS/cm), and can be measured using a conductivity meter sold, e.g., by Orion. The conductivity of a solution may be altered by changing the concentration of ions therein. For example, the concentration of a buffering agent and/or concentration of a salt (e.g. NaCl or KCl) in the solution may be altered in order to achieve the desired conductivity. Preferably, the salt concentration of the various buffers is modified to achieve the desired conductivity as in the Example below.

By "purifying" a polypeptide from a composition comprising the polypeptide and one or more contaminants is meant increasing the degree of purity of the polypeptide in the composition by removing (completely or partially) at least one contaminant from the composition. A "purification step" may be part of an overall purification process resulting in a "homogeneous" composition, which is used herein to refer to a composition comprising at least about 70% by weight of the polypeptide of interest, based on total weight of the composition, preferably at least about 80% by weight.

Unless indicated otherwise, the term "HER2" when used herein refers to human HER2 protein and "HER2" refers to human HER2 gene. The human HER2 gene and HER2 protein are described in Semba et al., *PNAS (USA)* 82:6497–6501 (1985) and Yamamoto et al. *Nature* 319:230–234 (1986) (Genebank accession number X03363), for example.

The term "humMAb4D5-8" when used herein refers to a humanized anti-HER2 antibody comprising the light chain amino acid sequence of SEQ ID NO:1 and the heavy chain amino acid sequence of SEQ ID NO:2 or amino acid sequence variants thereof which retain the ability to bind HER2 and inhibit growth of tumor cells which overexpress HER2 (see U.S. Pat. No. 5,677,171; expressly incorporated herein by reference).

The "pI" or "isoelectric point" of a polypeptide refer to the pH at which the polypeptide's positive charge balances its negative charge. pI can be calculated from the net charge of the amino acid residues of the polypeptide or can be determined by isoelectric focussing (e.g. using CSx chromatography as in the Example below).

By "binding" a molecule to an ion exchange material is meant exposing the molecule to the ion exchange material under appropriate conditions (pH/conductivity) such that the molecule is reversibly immobilized in or on the ion exchange material by virtue of ionic interactions between the molecule and a charged group or charged groups of the ion exchange material.

By "washing" the ion exchange material is meant passing an appropriate buffer through or over the ion exchange material.

To "elute" a molecule (e.g. polypeptide or contaminant) from an ion exchange material is meant to remove the molecule therefrom by altering the ionic strength of the buffer surrounding the ion exchange material such that the buffer competes with the molecule for the charged sites on the ion exchange material.

"Treatment" refers to both therapeutic treatment and prophylactic or preventative measures. Those in need of treatment include those already with the disorder as well as those in which the disorder is to be prevented.

A "disorder" is any condition that would benefit from treatment with the polypeptide purified as described herein. This includes chronic and acute disorders or diseases including those pathological conditions which predispose the mammal to the disorder in question.

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (TAXOL™, Bristol-Myers Squibb Oncology, Princeton, N.J.), and doxetaxel, toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors, such as tamoxifen and onapristone.

MODES FOR CARRYING OUT THE INVENTION

The invention herein provides a method for purifying a polypeptide from a composition (e.g. an aqueous solution) comprising the polypeptide and one or more contaminants. The composition is generally one resulting from the recombinant production of the polypeptide, but may be that resulting from production of the polypeptide by peptide synthesis (or other synthetic means) or the polypeptide may be purified from a native source of the polypeptide. Preferably the polypeptide is an antibody, e.g. one which binds the HER2 antigen.

For recombinant production of the polypeptide, the nucleic acid encoding it is isolated and inserted into a replicable vector for further cloning (amplification of the DNA) or for expression. DNA encoding the polypeptide is readily isolated and sequenced using conventional procedures (e.g., where the polypeptide is an antibody by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g. as described in U.S. Pat. No. 5,534,615, specifically incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; Kluyveromyces hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; yarrowia (EP 402,226); *Pichia pastoris* (EP 183,070); Candida; *Trichoderma reesia* (EP 244,234); *Neurospora crassa*; Schwanniomyces such as *Schwanniomyces occidentalis*; and filamentous fungi such as, e.g., Neurospora, Penicillium, Tolypocladium, and Aspergillus hosts such as *A. nidulans* and *A. niger*.

Suitable host cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

The host cells used to produce the polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells.

In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927, 762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the polypeptide can be produced intracellularly, in the periplasmic space, or directly secreted into the medium. If the polypeptide is produced intracellularly, as a first step, the particulate debris, either host cells or lysed cells (e.g. resulting from homogenization), is removed, for example, by centrifugation or ultrafiltration. Where the polypeptide is secreted into the medium, supernatants from such expression systems are generally first concentrated using a commercially available protein concentration filter, for example, an Amicon or Millipore Pellicon ultrafiltration unit.

The polypeptide is then subjected to one or more purification steps, including the ion exchange chromatography method as claimed herein. Examples of additional purification procedures which may be performed prior to, during, or following the ion exchange chromatography method include fractionation on a hydrophobic interaction chromatography (e.g. on phenyl sepharose), ethanol precipitation, isoelectric focusing, Reverse Phase HPLC, chromatography on silica, chromatography on HEPARIN SEPHAROSE™, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g. using protein A, protein G, an antibody, a specific substrate, ligand or antigen as the capture reagent).

Ion exchange chromatography is performed as claimed herein. A decision is first made as to whether an anion or cation exchange resin is to be employed. In general, a cation exchange resin may be used for polypeptides with pIs greater than about 7 and an anion exchange resin may be used for polypeptides with pIs less than about 7.

The anion or cation exchange resin is prepared according to known methods. Usually, an equilibration buffer is passed through the ion exchange resin prior to loading the composition comprising the polypeptide and one or more contaminants onto the resin. Conveniently, the equilibration buffer is the same as the loading buffer, but this is not required.

The various buffers used for the chromatography depend, for example, on whether a cation or anion exchange resin is employed. This is shown more clearly in the flow diagrams of FIGS. 1 and 2.

With particular reference to FIG. 1, which shows exemplary steps to be performed where a cation exchange resin is used, the pH and/or conductivity of each buffer is/are increased relative to the preceding buffer, except for the wash buffer where the conductivity and/or pH is/are less than the conductivity and/or pH of the preceding intermediate buffer. The aqueous solution comprising the polypeptide of interest and contaminant(s) is loaded onto the cation exchange resin using the loading buffer that is at a pH and/or conductivity such that the polypeptide and the contaminant bind to the cation exchange resin. As in the Example below, the loading buffer may be at a first low conductivity (e.g. from about 5.2 to about 6.6 mmhos). An exemplary pH for the loading buffer may be about 5.0 (see FIG. 1). From about 20 mg/mL to about 35 mg/mL of the polypeptide (e.g. of a full length antibody) may, for example, be loaded on the ion exchange resin.

The cation exchange resin is then washed with an intermediate buffer which is at a second conductivity and/or pH so as to essentially elute the contaminant, but not a substantial amount of the polypeptide of interest. This may be achieved by increasing the conductivity or pH, or both, of the intermediate buffer. The change from loading buffer to intermediate buffer may be step-wise or gradual as desired. In the Example herein, the intermediate buffer had a greater conductivity than that of the loading buffer (i.e. the intermediate buffer's conductivity was in the range from about 7.3 to about 8.4 mmhos). Alternatively, as shown in FIG. 1, the pH of the intermediate buffer may exceed that of the loading buffer in this embodiment of the invention, where a cation exchange resin is used. For example, the intermediate buffer may have a pH of about 5.4.

Following washing with the intermediate buffer, the cation exchange resin is washed or re-equilibrated with the wash buffer which has a conductivity or pH, or both, which is/are less than that of the intermediate buffer (i.e. the conductivity, or pH, or both, is/are changed in an opposite, i.e. reverse, direction to the preceding step, unlike ion exchange chromatography steps in the literature). In the Example below, the wash buffer had about the same conductivity as the loading buffer (i.e. in the range from about 5.2 to about 6.6 mmhos) and its conductivity was, therefore, less than that of the intermediate buffer. In another embodiment, one may reduce the conductivity of the wash buffer to a conductivity that is less than, or greater than, that of the loading buffer, provided the conductivity of the wash buffer is less than that of the intermediate buffer. In another embodiment, the pH of the wash buffer may be less than the pH of the intermediate buffer (e.g. the pH of the wash buffer may about 5.0). The change in conductivity and/or pH of the wash buffer compared to the intermediate buffer may be achieved by step-wise or gradual change of either or both of these parameters.

After the wash step of the preceding paragraph, the cation exchange resin is prepared for elution of the desired polypeptide molecule therefrom. This is achieved using an elution buffer that has a pH and/or conductivity such that the desired polypeptide no longer binds to the cation exchange resin and therefore is eluted therefrom. The pH and/or conductivity of the elution buffer generally exceed(s) the pH and/or conductivity of the loading buffer, the intermediate buffer and the wash buffer used in the previous steps. In the Example below, the conductivity of the elution buffer was in the range from about 10.0 to about 11.0 mmhos. Alternatively, or in addition, the pH of the elution buffer may be increased relative to the wash buffer and to the intermediate buffer (for example, the pH of the elution buffer may about 6.0). The change in conductivity and/or pH may be step-wise or gradual, as desired. Hence, the desired polypeptide is retrieved from the cation exchange resin at this stage in the method.

In an alternative embodiment, the ion exchange material comprises an anion exchange resin. This embodiment of the invention is depicted in FIG. 2 herein. As illustrated in this figure, the changes in conductivity are generally as described above with respect to a cation exchange resin. However, the direction of change in pH is different for an anion exchange resin. For example, if elution of the contaminant(s) and polypeptide are to be achieved by altering pH, the loading buffer has a first pH and the pH is decreased in the intermediate buffer so as to elute the contaminant or contaminants. In the third step, the column is washed/re-equilibrated with the wash buffer and the change in conductivity or pH, or both, is in the opposite direction to that of the previous step. Hence, the pH may be increased in the wash buffer, compared to the intermediate buffer. Following this step, the polypeptide of interest is eluted from the anion exchange resin using an elution buffer at a fourth conductivity and/or pH. If pH is altered, it will normally be less than the pH of the loading buffer, the intermediate buffer and the wash buffer. The change in pH and/or conductivity in progressive buffers can, as explained above, be step-wise or gradual.

In the preferred embodiment of the invention, a single parameter (i. e. either conductivity or pH) is changed to achieve elution of both the polypeptide and contaminant, while the other parameter (i.e. pH or conductivity, respectively) remains about constant. For example, while the conductivity of the various buffers (loading buffer, intermediate buffer, wash buffer and/or elution buffer) may differ, the pH's thereof may be essentially the same.

In an optional embodiment of the invention, the ion exchange resin is regenerated with a regeneration buffer after elution of the polypeptide, such that the column can be re-used. Generally, the conductivity and/or pH of the regeneration buffer is/are such that substantially all contaminants and the polypeptide of interest are eluted from the ion exchange resin. Generally, the regeneration buffer has a very high conductivity for eluting contaminants and polypeptide from the ion exchange resin.

The method herein is particularly useful for resolving a polypeptide molecule of interest from at least one contaminant, where the contaminant and polypeptide molecule of interest differ only slightly in ionic charge. For example, the pIs of the polypeptide and contaminant may be only "slightly different", for example they may differ by only about 0.05 to about 0.2 pI units. In the Example below, this method could be used to resolve an anti-HER2 antibody having a pI of 8.87, from a singly-deamidated variant thereof having a pI of 8.79. Alternatively, the method may be used to resolve a deamidated DNase, for example, from nondeamidated DNase. In another embodiment, the method may be used to resolve a polypeptide from a glycosylation variant thereof, e.g. for resolving a variant of a polypeptide having a different distribution of sialic acid compared to the nonvariant polypeptide.

The polypeptide preparation obtained according to the ion exchange chromatography method herein may be subjected to additional purification steps, if necessary. Exemplary further purification steps have been discussed above.

Optionally, the polypeptide is conjugated to one or more heterologous molecules as desired. The heterologous molecule may, for example, be one which increases the serum half-life of the polypeptide (e.g. polyethylene glycol, PEG), or it may be a label (e.g. an enzyme, fluorescent label and/or radionuclide) or a cytotoxic molecule (e.g. a toxin, chemotherapeutic drug, or radioactive isotope etc).

A therapeutic formulation comprising the polypeptide, optionally conjugated with a heterologous molecule, may be prepared by mixing the polypeptide having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. "Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG) The humMAb4D5-8 antibody of particular interest herein may be prepared as a lyophilized formulation, e.g. as described in WO 97/04801; expressly incorporated herein by reference.

The formulation herein may also contain more than one active compound as necessary for the particular indication being treated, preferably those with complementary activities that do not adversely affect each other. Such molecules are suitably present in combination in amounts that are effective for the purpose intended. For example, for an anti-HER2 antibody a chemotherapeutic agent, such as a taxoid or tamoxifen, may be added to the formulation.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulation to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide variant, which matrices are in the form of shaped articles, e.g., films, or microcapsule. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The polypeptide purified as disclosed herein or the composition comprising the polypeptide and a pharmaceutically acceptable carrier is then used for various diagnostic, therapeutic or other uses known for such polypeptides and compositions. For example, the polypeptide may be used to treat a disorder in a mammal by administering a therapeutically effective amount of the polypeptide to the mammal.

The following examples are offered by way of illustration and not by way of limitation. The disclosures of all citations in the specification are expressly incorporated herein by reference.

EXAMPLE 1

Full length human IgG rhuMAb HER2 (humAb4D5-8 in Carter et al. *Proc. Natl. Acad. Sci.* 89: 4285–4289 (1992) comprising the light chain amino acid sequence of SEQ ID NO:1 and heavy chain amino acid sequence of SEQ ID NO:2) was produced recombinantly in CHO cells. Following protein production and secretion to the cell culture medium, the CHO cells were separated from the cell culture medium by tangential flow filtration (PROSTACK™). Protein A chromatography was then performed by applying the Harvested Cell Culture Fluid (HCCF) from the CHO cells directly to an equilibrated PROSEP A™ column (Bioprocessing, Ltd).

Following Protein A chromatography, cation exchange chromatography was performed using a sulphopropyl (SP)-SEPHAROSE FAST FLOW™ (SPSFF) column (Pharmacia) to further separate the desired anti-HER2 antibody molecule. The chromatography operation was performed in bind and elute mode.

The SPSFF column was prepared for load by sequential washes with regeneration buffer (0.025 M MES/1.0 M NaCl, pH 5.6) followed by equilibration buffer (0.025 M MES/50 mM NaCl, pH 5.6). The column was then loaded with Protein A pool adjusted to a pH of 5.60±0.05 and a conductivity of 5.8±0.2 mmhos. Prior to elution, the column was washed in three steps: (1) loading buffer (0.025 M MES/50 mM NaCl, pH 5.6) for a minimum of 1 column volume; (2) intermediate buffer (0.025 M MES/70 mM NaCl, pH 5.6) until an apex of a 280 nm peak was reached; and (3) wash buffer (0.025 M MES/50 mM NaCl, pH 5.6) for a minimum of 1.2 column volumes. rhuMAb HER2 was then eluted from the column with elution buffer (0.025 M MES/95 mM NaCl, pH 5.6). The elution 280 nm profile has a shoulder on the leading edge (FIG. 3). At the inflection point of this shoulder, pooling starts and continues for an additional 5 column volumes. The column was then regenerated with regeneration buffer (0.025 M MES/1.0 M NaCl, pH 5.6).

Materials and Methods

Column and Load Preparation:

A reduced-scale SPSFF column was packed. The dimensions were: 27.0 mL volume, 1.0 cm diameter and 34.5 cm bed height. The pH of an aliquot of Protein A pool was titered to 5.6 with 1.5 M Tris base. The conductivity of the pool was reduced by the addition of an equal volume of sterile water for injection (SWFI).

Chromatography:

The chromatography runs for this study were performed with Pharmacia's UNICORN™ FPLC system. The equilibration, load, and initial wash steps were performed at a linear flow rate of 200 cm/h. All chromatography steps were performed at a linear flow rate of 100 cm/h. The sequence of chromatography steps are defined in Table 1. A total of six chromatography runs were performed with load densities of 15, 20, 25, 30, 35, and 40 mg of rhuMAb HER2 per mL of SPSFF resin.

TABLE 1

Chromatography Steps[1]

| Chromatography Step | Buffer | Approximate Endpoint |
| --- | --- | --- |
| Equilibration: Part 1 | 0.025M MES/1.0M NaCl, pH 5.6 | 2 CV[2] |
| Equilibration: Part 2 | 0.025M MES/0.05M NaCl, pH 5.6 | pH: 5.6 ± 0.1 Cond.: 5.8 ± 0.2 mmhos |
| Load | Adjusted Protein A Pool | As Required |
| Wash 1 | 0.025M MES/0.05M NaCl, pH 5.6 | 1.5 CV |
| Wash 2 | 0.025M MES/0.07M NaCl, pH 5.6 | Apex of Peak |
| Wash 3 | 0.025M MES/0.05M NaCl, pH 5.6 | 2 CV |
| Elution: Prepool | 0.025M MES/0.095M NaCl, pH 5.6 | To Leading Shoulder's Inflection Point (~1.2 CV) |
| Elution: Pool | 0.025M MES/0.095M NaCl, pH 5.6 | 5 CV |
| Regeneration | 0.025M MES/1.0M NaCl, pH 5.6 | 2 CV |

[1]The equilibration of the resin was performed in manual mode; the remaining steps were executed from a Pharmacia Unicom Program.
[2]CV = column volume(s).

Total Protein:

The protein concentration of each chromatography fraction (flow through, wash steps, elution prepool, elution pool, and regeneration) was determined by spectrophometric scans of each sample. The results were used to calculate product recovery yields. The extinction coefficient for rhuMAb HER2 is 1.45. Calculations used to derive the results (FIG. 4) are:

$$\text{Protein Concentration (mg/mL)} = \frac{280 \text{ nm}}{1.45} \times \text{Dilution Factor}$$

Protein Mass (mg) in Each Fraction = Protein Concentration (mg/mL) × Fraction Volume (mL)

$$\text{Yield (\%)} = \frac{\text{Fraction Mass (mg)}}{\text{Total Mass (mg)}} \times 100$$

Determination of rhuMAb HER2 Antibody Variants (CSx HPIEX):

The rhuMAb HER2 SPSFF chromatography column resolves antibody variants. Fractions from each of the study chromatographies were tested for the relative amount of variant antibody by CSx HPIEX chromatography. A BAKERBOND WIDE-PORET™ CSx HPIEX column (4.6×250 mm) was run at 1 mL/min at 55° C. The mobile phase was formed from a tertiary gradient (Table 2).

TABLE 2

Gradient Scheme

| Time (min) | % A | % B | % C |
| --- | --- | --- | --- |
| 0-Initial Conditions | 49 | 1 | 50 |
| 10.0 | 40 | 10 | 50 |
| 50.0 | 33 | 17 | 50 |
| 50.2 | 49 | 1 | 50 |
| 70.0 | 49 | 1 | 50 |

The column is run at 1 ml/min at 55° C.

The A buffer was 0.025 M MES, pH 5.9; the B buffer was 1 M Ammonium Acetate, pH 7.0; and the C solution was sterile water for injection. The column was equilibrated with the gradient's initial conditions (49% A; 1% B; and 50% C) and 200 µl of sample, diluted. with SWFI and containing <300 µg protein, was injected. Each resulting chromatogram was integrated to determine the percent area of each peak for each fraction (Table 3 and FIG. 5).

TABLE 3

CSx HPIEX analysis of rhuMAb HER2

| CSx Peak | rhuMAb HER2 Variant |
| --- | --- |
| a & b | Light Chain: Asn→Asp$^{30}$ deamidation -and- Other unidentifiable variation by tryptic map |
| 1 | Light Chain: Asn→Asp$^{30}$ deamidation |
| 3 | Fully Processed Antibody |
| 4 | Heavy Chain: Asp→Iso-Asp$^{102}$ -and/or- Heavy Chain: An Additional Lys$^{450}$ |
| Others | Heavy Chain: Asp→Succinimide$^{102}$ -and/or- Multiple permutations found in Peaks 1 and 4 |

Chromatograms Compared:

The absorbance data (AU 280 nm) from each chromatography file was exported from Unicorn in ASCII format. The data from the 0.025 M MES/0.07 M NaCl, pH 5.6 wash was translated into Excel format and copied into KALEIDA-GRAPH™. Using KALEIDAGRAPH™, the wash profiles were overlaid (FIG. 6) and compared to each other.

RESULTS AND DISCUSSION

Deamidated and other acidic variants of rhuMAb HER2 were produced when the antibody was made by recombinant DNA technology (see e.g., CSx peaks a, b and 1 in FIG. 5). The deamidated and other acidic variants constituted about 25% (calculated as area under the integrated curve or profile obtained by CSx chromatography) of the composition obtained from the initial Protein A chromatography step. It was discovered that the ion exchange method described herein could be used to substantially reduce the amount of deamidated and other acidic variants in the anti-HER2 composition, i.e. to about 13% or less (i.e. the amount of acidic variants in the preparation subjected to cation exchange chromatography as described herein was decreased by about 50% or more).

An absorbance trace from a cation exchange column run performed as described above is shown in FIG. 3. This method resolved a deamidated variant of anti-HER2 antibody that differed only slightly from nondeamidated anti-HER2 antibody. The increase in conductivity from the initial conditions to the intermediate wash began to elute the deamidated anti-HER2 antibody. However, continued washing at this conductivity was found to elute nondeamidated anti-HER2 antibody, resulting in a loss of product. Proceeding directly from the intermediate buffer to the elution buffer was observed to result in either an unacceptably low removal of deamidated anti-HER2 antibody from the product if pooling began early or unacceptably low yields of anti-HER2 antibody product if pooling was delayed until the deamidated anti-HER2 antibody was reduced. It was discovered that by going back to lower conductivity as used initially, the elution of deamidated anti-HER2 antibody continued, without significant anti-HER2 antibody product elution.

The effect of rhuMAb HER2 load on (a) buffer requirements, (b) product recovery in the pool, and (c) product quality in the pool was evaluated.

At load densities of 15 mg/mL up to 35 mg/mL, the product yield in the elution pool is approximately 75%. For the load density of 40 mg/mL, the product yield in the pool dropped to 65% (FIG. 4). This reduced recovery in the pool is largely attributed to an increased antibody in the two wash steps (at 70 mM NaCl and 50 mM NaCl, respectively).

The quality of rhuMAb HER2 in all the elution pools is equivalent as determined by CSx HPIEX analysis (FIG. 5). Compared to the load material; there is an enrichment of the nondeamidated antibody (Peak 3), no change in the amount Iso-Asp$^{102}$ or Lys$^{450}$ antibody (Peak 4), and a reduction of the amount of Asp$^{30}$ deamidated antibody (Peaks a, b, 1 and others).

The quality of rhuMAb HER2 in these cation pools is improved through the intermediate wash step. As the mass of rhuMAb HER2 bound to the resin increases, the intermediate buffer volume consumption needed to reach the apex of the 280 nm peak decreases. The buffer volume required for a 40 mg/mL load density is approximately 2.5 column volumes. The buffer volume required for a 15 mg/mL load density is approximately 15 column volumes. The exact increase of buffer requirement is not linear with the 5 mg/mL incremental changes between these two extremes. The greatest increase is seen between the load densities of 20 mg/mL and 15 mg/mL. Here the requirement doubles from 7.5 column volumes to the previously mentioned 15 column volumes of buffer. If the apex of the 70 mM NaCl wash peak is reached, however, the product quality is equivalent for any of load densities examined.

This study determined how much rhuMAb HER2 can be loaded onto the SPSFF resin. Between the ranges of 15 to 40 mg of antibody per mL of resin, there is no difference in the quality of rhuMAb HER2 recovered in the elution pool. The quantity of rhuMAb HER2 recovered, however, is reduced by approximately 10% when the resin is loaded with greater than 35 mg/mL. For consistent yields it is recommended that 35 mg/mL be set as the maximum load for manufacture of rhuMAb HER2. Furthermore, due to the substantial increase in the 70 mM NaCl wash volume requirement between the 20 and 15 mg/mL; it is recommended that 20 mg/mL be set as the minimal load for manufacture of rhuMAb HER2.

What is claimed is:

1. A composition comprising a mixture of anti-HER2 antibody and one or more acidic variants thereof, wherein the amount of the acidic variant(s) is less than about 25%.

2. The composition of claim 1 further comprising a pharmaceutically acceptable carrier.

3. The composition of claim 1 wherein the anti-HER2 antibody is humMAb4D5-8.

* * * * *

SEQUENCE LISTING

```
<160> NUMBER OF SEQ ID NOS: 2

<210> SEQ ID NO 1
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Arg Ser Gly Thr Asp Phe Thr Leu Thr Ile
                65                  70                  75
```

```
Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                 100                 105

Ile Lys Arg Thr Val Ala Ala Pro Ser Val Phe Ile Phe Pro Pro
               110                 115                 120

Ser Asp Glu Gln Leu Lys Ser Gly Thr Ala Ser Val Val Cys Leu
               125                 130                 135

Leu Asn Asn Phe Tyr Pro Arg Glu Ala Lys Val Gln Trp Lys Val
               140                 145                 150

Asp Asn Ala Leu Gln Ser Gly Asn Ser Gln Glu Ser Val Thr Glu
               155                 160                 165

Gln Asp Ser Lys Asp Ser Thr Tyr Ser Leu Ser Ser Thr Leu Thr
               170                 175                 180

Leu Ser Lys Ala Asp Tyr Glu Lys His Lys Val Tyr Ala Cys Glu
               185                 190                 195

Val Thr His Gln Gly Leu Ser Ser Pro Val Thr Lys Ser Phe Asn
               200                 205                 210

Arg Gly Glu Cys
```

<210> SEQ ID NO 2
<211> LENGTH: 449
<212> TYPE: PRT
<213> ORGANISM: Artificial sequence
<220> FEATURE:
<223> OTHER INFORMATION: Sequence is synthesized.

<400> SEQUENCE: 2

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Asn Ile Lys
                 20                  25                  30

Asp Thr Tyr Ile His Trp Val Arg Gln Ala Pro Gly Lys Gly Leu
                 35                  40                  45

Glu Trp Val Ala Arg Ile Tyr Pro Thr Asn Gly Tyr Thr Arg Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ser Arg Trp Gly Gly Asp Gly Phe Tyr
                 95                 100                 105

Ala Met Asp Tyr Trp Gly Gln Gly Thr Leu Val Thr Val Ser Ser
                110                 115                 120

Ala Ser Thr Lys Gly Pro Ser Val Phe Pro Leu Ala Pro Ser Ser
                125                 130                 135

Lys Ser Thr Ser Gly Gly Thr Ala Ala Leu Gly Cys Leu Val Lys
                140                 145                 150

Asp Tyr Phe Pro Glu Pro Val Thr Val Ser Trp Asn Ser Gly Ala
                155                 160                 165

Leu Thr Ser Gly Val His Thr Phe Pro Ala Val Leu Gln Ser Ser
                170                 175                 180

Gly Leu Tyr Ser Leu Ser Ser Val Val Thr Val Pro Ser Ser Ser
                185                 190                 195
```

-continued

```
Leu Gly Thr Gln Thr Tyr Ile Cys Asn Val Asn His Lys Pro Ser
                200                 205                 210
Asn Thr Lys Val Asp Lys Lys Val Glu Pro Lys Ser Cys Asp Lys
                215                 220                 225
Thr His Thr Cys Pro Pro Cys Pro Ala Pro Glu Leu Leu Gly Gly
                230                 235                 240
Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn
                290                 295                 300
Ser Thr Tyr Arg Val Val Ser Val Leu Thr Val Leu His Gln Asp
                305                 310                 315
Trp Leu Asn Gly Lys Glu Tyr Lys Cys Lys Val Ser Asn Lys Ala
                320                 325                 330
Leu Pro Ala Pro Ile Glu Lys Thr Ile Ser Lys Ala Lys Gly Gln
                335                 340                 345
Pro Arg Glu Pro Gln Val Tyr Thr Leu Pro Pro Ser Arg Glu Glu
                350                 355                 360
Met Thr Lys Asn Gln Val Ser Leu Thr Cys Leu Val Lys Gly Phe
                365                 370                 375
Tyr Pro Ser Asp Ile Ala Val Glu Trp Glu Ser Asn Gly Gln Pro
                380                 385                 390
Glu Asn Asn Tyr Lys Thr Thr Pro Pro Val Leu Asp Ser Asp Gly
                395                 400                 405
Ser Phe Phe Leu Tyr Ser Lys Leu Thr Val Asp Lys Ser Arg Trp
                410                 415                 420
Gln Gln Gly Asn Val Phe Ser Cys Ser Val Met His Glu Ala Leu
                425                 430                 435
His Asn His Tyr Thr Gln Lys Ser Leu Ser Leu Ser Pro Gly
                440                 445
```